(12) United States Patent
Skibin et al.

(10) Patent No.: US 8,444,315 B2
(45) Date of Patent: May 21, 2013

(54) METHOD OF DETERMINING THERMOPHYSICAL PROPERTIES OF SOLID BODIES

(75) Inventors: Alexander Petrovich Skibin, Moscow (RU); Yury Anatolievich Popov, Moscow (RU); Daria Aleksandrovna Mustafina, Perm (RU); Valery Vasilievich Shako, Domodedovo (RU)

(73) Assignee: Schlumberger Technology Corporation, Sugar Land, TX (US)

( * ) Notice: Subject to any disclaimer, the term of this patent is extended or adjusted under 35 U.S.C. 154(b) by 632 days.

(21) Appl. No.: 12/570,811

(22) Filed: Sep. 30, 2009

(65) Prior Publication Data

US 2010/0080260 A1    Apr. 1, 2010

(30) Foreign Application Priority Data

Sep. 30, 2008    (RU) .................. 2008138643

(51) Int. Cl.
*G01N 25/00* (2006.01)
*G01K 3/00* (2006.01)

(52) U.S. Cl.
USPC ............ 374/44; 374/43; 374/110; 374/167; 374/137

(58) Field of Classification Search
USPC ................ 374/43, 44, 110, 137, 167
See application file for complete search history.

(56) References Cited

U.S. PATENT DOCUMENTS

| | | | | |
|---|---|---|---|---|
| 3,761,713 A | * | 9/1973 | Merrill | 374/124 |
| 3,864,969 A | * | 2/1975 | Smith, Jr. | 73/152.13 |
| 4,120,199 A | * | 10/1978 | Mufti | 73/152.12 |
| 4,343,181 A | * | 8/1982 | Poppendiek | 73/152.13 |
| 4,933,887 A | * | 6/1990 | Danko et al. | 702/136 |
| 4,947,682 A | * | 8/1990 | Anderson et al. | 73/152.12 |
| 5,159,569 A | * | 10/1992 | Xu et al. | 702/13 |
| 5,346,307 A | * | 9/1994 | Ramirez et al. | 374/136 |
| 2006/0185843 A1 | * | 8/2006 | Smith, Jr. | 166/250.01 |
| 2008/0073122 A1 | * | 3/2008 | Blanz et al. | 175/50 |
| 2011/0156707 A1 | * | 6/2011 | Popov et al. | 324/324 |

FOREIGN PATENT DOCUMENTS

| | | |
|---|---|---|
| RU | 2011977 C1 | 4/1994 |
| RU | 2153664 C1 | 7/2000 |

OTHER PUBLICATIONS

Beck et al., "Inverse Heat Conduction: Ill-Posed Problems," New York: Wiley-Interscience Publication, 1989: p. 312.
Popov, "Some Peculiarities of Rocks' Heat Conduction," Proceedings of Higher Education Institutions, Geology and Survey, 1984, No. 4: pp. 72-76.
Glasko, "Mathematical specifics of inverse problems," Inverse Problems of Mathematical Physics, American Institute of Physics: New York, 1988: pp. 5-7.

* cited by examiner

*Primary Examiner* — Mirellys Jagan

(57) ABSTRACT

The invention is related to methods for determining thermophysical properties of solid bodies, particularly, to methods for determining thermal conductivity and volumetric heat capacity. In accordance with the method, a reference sample and sequentially located samples of solid bodies are heated by a thermal energy source moving at a constant speed relative to the reference sample and the samples being studied. Excessive temperatures of the surfaces of the reference sample and the studied samples at points on a line of heating are measured and the thermophysical properties of the reference sample and the samples being studied are determined. Arbitrary shape samples are used and thermal conductivity and volumetric heat capacity of the samples are determined by solving an inverse coefficient problem of thermal conductivity.

2 Claims, 1 Drawing Sheet

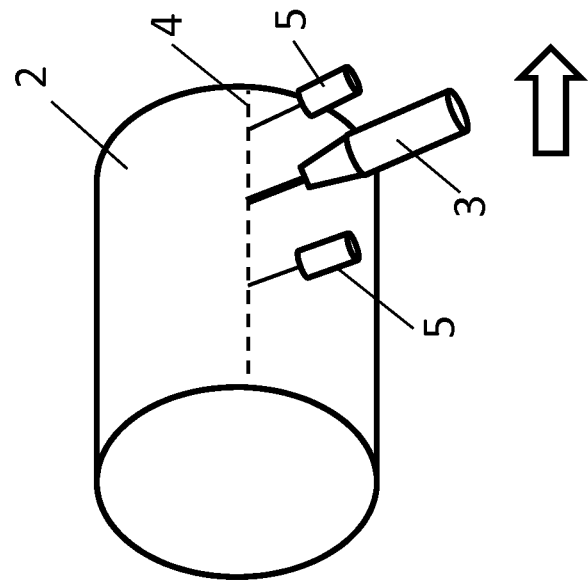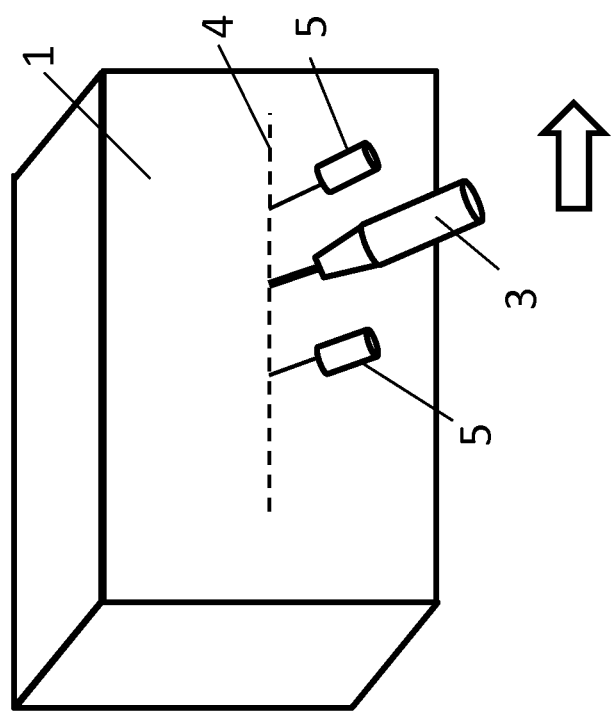

METHOD OF DETERMINING THERMOPHYSICAL PROPERTIES OF SOLID BODIES

TECHNICAL FIELD

This invention is related to methods for determining thermophysical properties of solid bodies (like rocks).

The correct record of the thermophysical properties of rocks, such as thermal conduction, thermal capacity and thermal diffusivity, becomes a top priority during industrial application of thermal production enhancement methods providing prior simulation of the reservoir (oil formation) and borehole heat-mass exchange processes as well as the borehole equipment thermal mode determination.

BACKGROUND

A proposed method of non-destructive determination of thermophysical properties of solid bodies differs from known methods (e.g., Patent RU 2153664 or Patent RU 2011977) by the possibility (1) to carry out measurements on short samples of arbitrary form, (2) to use only one reference sample, (3) to enhance measurement functionalities by measuring volumetric heat capacity, and (4) to increase measurement accuracy as compared with existing methods, which have systematic errors because of surface curvature of samples.

SUMMARY

The invention provides for expanded functionalities by ensuring volumetric heat capacity measurements and improving measurement accuracy.

The proposed method of determining thermophysical properties of solid bodies, including bodies with non-uniform properties, includes heating a sample surface using a thermal energy source. The thermal energy source is moved relative to the sample and excessive temperatures on the surface of the sample are determined. The thermophysical properties, like thermal conductivity and/or thermal diffusivity, are determined based on the excessive temperatures. The method may be used for the samples of any shape and ensures wide-range of thermal conductivity measurements (from 0.06 to 250 W/(mK).

BRIEF DESCRIPTION OF THE DRAWINGS

Further on, the invention is explained by a description of its preferred embodiments, with references to associated drawing illustrating an example system that can implement embodiments of non destructive determination of thermophysical properties of solid bodies.

DETAILED DESCRIPTION

The method of determining thermophysical properties of solid bodies includes heating a surface of a reference sample 1 using a thermal energy source 3. The reference sample is a uniform sample with fixed dimensions, with a known constant thermal conductivity, and a known volumetric heat capacity. The method further includes heating surfaces of sequentially located samples of the solid bodies 2 using the thermal energy source 3 (Popov Yu. A., Some Peculiarities of Rocks' Heat Conduction, Universities' Proceedings, Geology and Exploration, No. 4-1984, pp. 72-76.). The thermal energy source 3 is moved with a constant speed relative to the reference sample 1 and the samples of the solid bodies 2 (direction of movement is shown by arrows). Temperature sensors 5 are used to measure excessive temperatures on the surface of the reference sample and the surfaces of the samples of solid bodies 2. The measurements are made at points on a heating line 4 (a line on a surface along which the thermal energy source centre is moving). An excessive temperature is the difference between a surface temperature of a sample during heating and an initial temperature of the surface before heating. The method includes determining the thermal conductivity of the samples based on the measurements of the excessive temperatures of the reference sample and the samples being studied.

While performing measurements on a standard core sample (a 30×30 mm cylindrical stick of rock) with the use of a flat reference sample, a theoretical simulation (the process study using theoretical models—in this case—using a numerical solution) of physical processes accompanying the measurement process is used for determination of the difference of excessive temperatures for the flat and cylindrical surfaces. Then, a set correction is applied to the measured excessive temperatures on the surfaces of the reference sample and the samples being studied.

While performing measurements on a standard core sample, an inverse coefficient problem of thermal conductivity is solved (see James V. Beck, Ben Blackwell, Charles R. St. Clair, Jr/Inverse Heat Conduction Ill-Posed Problems: Wiley Interscience Publication N.Y. 1989-312 p.). Thermal conductivity coefficients and volumetric heat capacity of the standard core cylindrical samples are determined using a solution of the inverse coefficient problem of thermal conductivity.

While performing measurements on flat samples, an inverse coefficient problem of thermal conductivity is solved. Thermal conductivity coefficients and volumetric heat capacity of the flat samples are determined using a solution of the inverse coefficient problem of thermal conductivity.

During the method implementation, a reference sample 1 and studied samples 2 are located on a desk (not shown). A laser 3 used as a thermal energy source is switched on heating mode and is moving linearly at a constant speed (2-4 mm/sec). The temperature measurements are carried out by sensors 5 in series on the surfaces of the reference sample and the samples being studied. Based on a solution of an inverse problem of thermal conductivity for the reference sample, a thermal energy distribution function of the thermal energy source is restored. Based on the solution of the inverse coefficient problem of thermal conductivity for the sample being studied, a thermal conductivity coefficient and a volumetric heat capacity are restored.

The invention claimed is:
1. A method of non-destructive determination of thermophysical properties of solid bodies, the method comprising:
   providing at least one arbitrary shape sample of a solid body,
   providing a uniform reference sample with fixed dimensions,
   disposing the at least one arbitrary shape sample in sequence with the reference sample,
   heating surfaces of the reference sample and the at least one arbitrary shape sample using a thermal energy source moving at a constant speed relative to the reference sample and the at least one arbitrary shape sample,
   measuring excessive temperatures of the surfaces of the reference sample and the at least one arbitrary shape sample at points on a line of heating, determining a thermal energy distribution function of the thermal energy source by solving an inverse thermal conductivity problem for the reference sample, and determining a thermal conductivity and a volumetric heat capacity of the at least one arbitrary shape sample by solving an inverse coefficient problem of thermal conductivity for the at least one arbitrary shape sample.

2. The method of claim 1 wherein the arbitrary shape samples of the solid bodies are core samples.

* * * * *